(12) United States Patent
Sarkar

(10) Patent No.: US 12,636,238 B2
(45) Date of Patent: May 26, 2026

(54) HYPOCHLOROUS ACID-BASED EYELID CLEANSERS

(71) Applicant: OCuSOFT, Inc., Rosenberg, TX (US)

(72) Inventor: Paramita Sarkar, Rosenberg, TX (US)

(73) Assignee: OCuSOFT, Inc., Rosenberg, TX (US)

( * ) Notice: Subject to any disclaimer, the term of this patent is extended or adjusted under 35 U.S.C. 154(b) by 238 days.

(21) Appl. No.: 18/756,974

(22) Filed: Jun. 27, 2024

(65) Prior Publication Data

US 2025/0000762 A1     Jan. 2, 2025

Related U.S. Application Data

(60) Provisional application No. 63/511,023, filed on Jun. 29, 2023.

(51) Int. Cl.
| | |
|---|---|
| *A61K 8/20* | (2006.01) |
| *A61K 8/36* | (2006.01) |
| *A61Q 19/10* | (2006.01) |

(52) U.S. Cl.
CPC .................. *A61K 8/20* (2013.01); *A61K 8/36* (2013.01); *A61Q 19/10* (2013.01)

(58) Field of Classification Search
CPC ............. A61K 8/20; A61K 8/36; A61Q 19/10
See application file for complete search history.

(56) References Cited

U.S. PATENT DOCUMENTS

| | | | | |
|---|---|---|---|---|
| 9,833,399 | B2 * | 12/2017 | Adkins, Jr. | .............. A61K 8/68 |
| 11,364,262 | B2 | 6/2022 | Almås | |

| | | | | |
|---|---|---|---|---|
| 2009/0192231 | A1 | 7/2009 | Lemons | |
| 2019/0336415 | A1 | 11/2019 | Adkins, Jr. et al. | |
| 2020/0146890 | A1 * | 5/2020 | Smith | ........................ A61F 9/04 |
| 2022/0211044 | A1 | 7/2022 | Alimi et al. | |
| 2025/0032428 | A1 * | 1/2025 | Adkins, Jr. | .......... A61K 31/047 |
| 2025/0302868 | A1 * | 10/2025 | Sarkar | .................. A61K 9/0048 |

FOREIGN PATENT DOCUMENTS

| | | | | |
|---|---|---|---|---|
| CN | 114028326 | A * | 2/2022 | ............. A61P 15/00 |
| WO | 2015/061632 | A2 | 4/2015 | |

OTHER PUBLICATIONS

CN114028326A (Li et al.); machine translation; published Feb. 11, 2022.*

* cited by examiner

*Primary Examiner* — Jeffrey T. Palenik

(74) *Attorney, Agent, or Firm* — D'Ambrosio & Menon, PLLC; Usha Menon

(57) ABSTRACT

An antimicrobial eyelid cleanser composition contains hypochlorous acid, sodium acetate and purified water. The composition has a free available chlorine (FAC) concentration of from about 10 ppm-300 ppm, an osmolality of 40-200 mOsm/kg and a viscosity of 1 cP-500 cP. The composition has a pH from about 3.5-6.5. The eyelid cleanser composition is an ophthalmic or ocular composition that can clean the eyelids and eyes and remove excessive oil, debris, and desquamated skin from the eyelids and surrounding areas while reducing inflammation and promoting wound healing.

12 Claims, No Drawings

HYPOCHLOROUS ACID-BASED EYELID CLEANSERS

CROSS-REFERENCE TO RELATED APPLICATIONS

This application claims the benefit of Provisional U.S. Patent Application No. 63/511,023 filed Jun. 29, 2023, the entire content and disclosure of which, both express and implied, is incorporated herein by reference.

FIELD OF THE INVENTION

The present invention relates generally to eyelid and skin cleaning compositions and to methods of preparing and using such compositions.

BACKGROUND

Ocular health includes not only the eyes themselves but also related structures, such as the eyelids. Playing a crucial role in maintaining overall eye health, eyelids protect the eyes from potential dangers like approaching objects and airborne contaminants, including pollen, dust, and other foreign substances. Eyelids house important glands, the lacrimal and meibomian glands, which produce layers of tear film essential for maintaining healthy eyes. Blinking forms a new layer of tear film and spreads tears evenly across the cornea, lubricating the eye's surface. Furthermore, this blinking action helps remove foreign materials from the eye.

Eyelid issues, although common, can be particularly troublesome for contact lens wearers and may potentially lead to more severe complications. One notable complication is blepharitis, which is a chronic inflammatory condition of the eyelids, characterized by a scaly crust along the lid margins. The underlying causes of blepharitis may include bacterial infections, allergies, or even an association with facial and scalp seborrhea. Effective treatment generally entails frequent eyelid cleansing to eliminate excess oil, debris, and desquamated skin, which could otherwise exacerbate the problem.

Blepharitis, an inflammation of the eyelid, is often accompanied by or secondary to an internal hordeolum, a bacterial infection affecting the skin's surface at the edge of the eyelid. Another related infection is an external hordeolum, more commonly known as a stye, which targets the small oil-secreting meibomian glands along the eyelid's edge, encircling the eyelashes. Styes usually manifest as red, tender bumps that fully develop within three days and are characterized by pain, redness, and tenderness of the eyelid margins. Regularly cleansing the eyelid margins can help minimize the occurrence of these often-recurring conditions. A chalazion, which is an inflammation of the meibomian glands inside the eyelid, is another issue to consider. Chalazia typically grow slowly over 2-3 weeks, and although they are not generally painful, they may necessitate surgical intervention if left untreated.

Enhancing eyelid hygiene with the use of cleansers can mitigate the severity of various problems, such as the ones mentioned earlier, and other medical complications like rosacea and seborrhea. By addressing these issues early, it may be possible to prevent them altogether. Eyelid cleansers serve a dual purpose, as they are effective in cleaning not only eyelashes and eyelids, but also the periocular area. Furthermore, they can be employed as a pre-operative scrub to diminish the presence of harmful bacteria, thus reducing the likelihood of infection, inflammation, or endophthalmitis in patients.

SUMMARY

According to an embodiment, the eyelid cleanser composition includes: from about 0.005 to about 0.05 wt. % hypochlorous acid; from about 0.001 to 2.0 wt. % sodium acetate; and purified water q.s. up to 100% w/w. The composition has a free available chlorine (FAC) concentration of from about 10 ppm-300 ppm. The composition has an osmolality of 40-200 mOsm/kg and a viscosity of 1 cP-500 cP. The composition has a pH from about 3.5-6.5.

According to an embodiment, the composition further includes from about 0.05 wt. % to about 0.75 wt. % sodium lauryl sulfate or sodium laureth sulfate and from about 0.001 wt. % to about 2.0 wt. % acetic acid.

According to another embodiment, the composition further comprises from about 0.05 wt. % to 0.75 wt. % capryl/caprylyl glucoside, from about 0.05 wt. % to about 1.0 wt. % propylene glycol, from about 0.001 wt. % to 2.0 wt. % acetic acid, from about 0.05 wt. % to about 5.0 wt. % medium chain alkanes.

According to yet another embodiment, the composition further comprises from about 0.05 wt. % to about 0.75 wt. % dioctyl sodium sulfocsuccinate, and from about 0.001 wt. % to about 2.0 wt. % acetic acid.

DETAILED DESCRIPTION

The term and phrases "invention," "present invention," "instant invention," and similar terms and phrases as used herein are non-limiting and are not intended to limit the present subject matter to any single embodiment, but rather encompass all possible embodiments as described.

As used herein, all weight percentages (wt. %) are based on the total wt. % of the skin care composition, unless otherwise specified. Additionally, all composition percentages are based on totals equal to 100 wt. %, unless otherwise specified.

The compositions and methods for their use can "comprise," "consist essentially of," or "consist of" any of the ingredients or steps disclosed throughout the specification. As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and can include the ingredients of the present invention and do not exclude other ingredients or elements described herein. The use of the word "a" or "an" when used in conjunction with the term "comprising" in the claims and/or the specification may mean "one," but it is also consistent with the meaning of "one or more," "at least one," and "one or more than one." As used herein, "consisting essentially of" means that the invention may include ingredients in addition to those recited in the claim, but only if the additional ingredients do not materially alter the basic and novel characteristics of the claimed invention. Generally, such additives may not be present at all or only in trace amounts. However, it may be possible to include up to about 10% by weight of materials that could materially alter the basic and novel characteristics of the invention as long as the utility of the composition (as opposed to the degree of utility) is maintained.

All ranges recited herein include the endpoints, including those that recite a range "between" two values. Terms such as "about," "generally," "substantially," and the like are to be construed as modifying a term or value such that it is not an absolute. Such terms will be defined by the circumstances and the terms that they modify as those terms are understood by those of skill in the art. In one non-limiting embodiment, the terms are defined to be within 5%. The term "substantially" and its variations are defined as being largely but not necessarily wholly what is specified as understood by one of ordinary skill in the art, and in one non-limiting embodiment substantially refers to ranges within 0.01%-5%.

As used herein, the term "effective amount" of a composition refers to an amount sufficient to elicit the desired biological response. As will be appreciated by those of ordinary skill in this art, and effective amount of a substance may vary depending on such factors as the desired biological endpoint, the patient, etc. The terms effective amount and clinically effect may be used interchangeably herein. For example, an effective amount/clinically effective amount of the composition is the amount that can be used facilitate long term eyelid hygiene while also substantially reducing inflammation and promoting wound healing of the eyelids.

While the specification concludes with the claims particularly pointing and distinctly claiming the invention, it is believed that the present invention will be better understood from the following description.

The eyelid cleanser composition is an ophthalmic or ocular composition that can clean the eyelids and eyes and remove excessive oil, debris, and desquamated skin from the eyelids and surrounding areas while reducing inflammation and promoting wound healing. The composition contains an aqueous vehicle containing hypochlorous acid, a buffer consisting of sodium acetate and acetic acid, with a final pH in the range of about 3.5 to about 6.5.

A hypohalous acid is an acid consisting of a halogen bound to a hydroxyl functional group. Preferably, the halogen is chlorine and the hypohalous acid is hypochlorous acid. The composition contains at least 50 to 500 ppm of hypochlorous acid.

Free available chlorine or free active chlorine (FAC) refers to the amount of chlorine that is available to disinfect or kill microorganisms. Importantly, FAC covers many forms of chlorine, such as hypochlorous acid and hypohalite anion, in addition to freely available chlorine. Measurement and quantification of FAC is typically accomplished by a titration or colorimetric method. In certain embodiments, the eyelid cleanser composition contains 10 to 300 ppm of free available chlorine (FAC).

Hypohalous acid compositions require buffering agents to maintain a stable pH during storage and application to the ocular area. The composition includes an acidic buffer consisting of a solution of sodium acetate and acetic acid. In exemplary embodiments, the concentration of sodium acetate in the composition is 0.001 to 2% w/w, while that of acetic acid is 0.001 to 2% w/w. These concentration ranges allow for the calculation of the necessary amounts of each buffering agent to achieve the desired pH value by those skilled in the art.

The composition can contain one or more surfactants to improve its cleansing ability by dissolving and removing oil, debris, and desquamated skin. Surfactants work by forming micelles when in contact with the surface of the skin. The micelles solubilize oil and trap debris and loose skin, which can subsequently be rinsed away. Some suitable surfactants include sodium lauryl sulfate, capryl/caprylyl glucoside, sodium laureth sulfate, dioctyl sodium sulfosuccinate, polyglyceryl-6 caprylate, polyglyceryl-4 caprate, and mixtures thereof. The total concentration of surfactants in the composition can range from 0.05% to 5% w/w.

An emollient is a substance that helps to soften and soothe the skin, making it more supple and smooth. Emollients are typically used in moisturizers, lotions, and balms to improve skin hydration and reduce the appearance of dryness and roughness. They work by forming a protective barrier on the surface of the skin that helps to lock in moisture and prevent water loss. They can be derived from natural sources, like Yucca plant extract, or they can be synthesized in a laboratory. The composition can contain one or more emollients chosen from the group of medium chain alkanes (C9 to C12), Yucca extract, and mixtures thereof. The total concentration of the one or more emollients is in the range of 0.05 to 8% w/w.

The composition can further include a humectant. A humectant is a substance that helps to retain moisture by attracting water molecules from the environment and holding them within the composition. In topological applications, humectants will attract moisture to the skin surface and retain water molecules just beneath the skin's surface. According to an embodiment, propylene glycol is utilized as a humectant in the eyelid cleanser composition in a concentration of 0.05 to 1% w/w.

The aqueous vehicle can be deionized water or purified water USP. The composition is physiologically compatible with viscosity, osmolality and pH in appropriate ranges. Osmolality can be adjusted using sugars, glycerin, propylene glycol and similar ingredients. The osmolality of the composition can be adjusted from about 40 mOsm/kg to about 200 mOsm/kg. Viscosity is similarly adjusted with viscosity modifiers (such as, without limitation, carboxymethyl cellulose, hydroxypropyl methylcellulose, Carbopol®). The viscosity of the composition is preferably greater in the range of 1 to 500 cP.

In one embodiment, the eyelid cleanser composition includes hypochlorous acid, sodium lauryl sulfate, an acidic buffer consisting of sodium acetate and acetic acid, and purified water. For example, in an exemplary embodiment, the eyelid cleanser includes 0.005-0.05% w/w hypochlorous acid, 0.05-0.75% w/w sodium lauryl sulfate, an acidic buffer consisting of 0.001-2.0% w/w sodium acetate and 0.001-2.0% w/w acetic acid, and purified water quantum sufficit, (q.s.) up to 100 w/w.

In another embodiment, the eyelid cleanser composition includes hypochlorous acid, capryl/caprylyl glucoside, propylene glycol, medium chain alkanes, an acidic buffer consisting of sodium acetate and acetic acid, and purified water. For example, in an exemplary embodiment, the eyelid cleanser includes 0.005-0.05% w/w hypochlorous acid, 0.05-0.75% w/w capryl/caprylyl glucoside, 0.05-1.0% w/w propylene glycol, 0.05-5.0% w/w medium chain alkanes, an acidic buffer consisting of 0.001-2.0% w/w sodium acetate and 0.001-2.0% w/w acetic acid, and purified water q.s. up to 100 w/w.

In one embodiment, the eyelid cleanser composition includes hypochlorous acid, sodium lauryl sulfate, capryl/caprylyl glucoside, medium chain alkanes, an acidic buffer consisting of sodium acetate and acetic acid, and purified water. For example, in an exemplary embodiment, the eyelid cleanser includes 0.005-0.05% w/w hypochlorous acid, 0.05-0.75% w/w sodium lauryl sulfate, 0.05-0.75% w/w capryl/caprylyl glucoside, 0.05-5.0% w/w medium chain alkanes, an acidic buffer consisting of 0.001-2.0% w/w sodium acetate and 0.001-2.0% w/w acetic acid, and purified water q.s. up to 100 w/w.

In one embodiment, the eyelid cleanser composition includes hypochlorous acid, sodium laureth sulfate, an acidic buffer consisting of sodium acetate and acetic acid, and purified water. For example, in an exemplary embodiment, the eyelid cleanser includes 0.005-0.05% w/w hypochlorous acid, 0.05-0.75% w/w sodium laureth sulfate, an acidic buffer consisting of 0.001-2.0% w/w sodium acetate and 0.001-2.0% w/w acetic acid, and purified water q.s. up to 100 w/w.

In one embodiment, the eyelid cleanser composition includes hypochlorous acid, dioctyl sodium sulfosuccinate, an acidic buffer consisting of sodium acetate and acetic acid, and purified water. For example, in an exemplary embodiment, the eyelid cleanser includes 0.005-0.05% w/w hypochlorous acid, 0.05-0.75% w/w dioctyl sodium sulfosuccinate, an acidic buffer consisting of 0.001-2.0% w/w sodium acetate and 0.001-2.0% w/w acetic acid, and purified water q.s. up to 100 w/w.

In one embodiment, the eyelid cleanser composition includes hypochlorous acid, polyglyceryl-6 caprylate and polyglyceryl-4 caprate, yucca extract, an acidic buffer consisting of sodium acetate and acetic acid, and purified water. For example, in an exemplary embodiment, the eyelid cleanser includes 0.005-0.05% w/w hypochlorous acid, 0.05-5% w/w polyglyceryl-6 caprylate and polyglyceryl-4 caprate, 0.05-3.0% w/w yucca extract, an acidic buffer consisting of 0.001-2.0% w/w sodium acetate and 0.001-2.0% w/w acetic acid, and purified water q.s. up to 100 w/w.

In one embodiment, the eyelid cleanser composition includes hypochlorous acid, medium chain alkanes, yucca extract, an acidic buffer consisting of sodium acetate and acetic acid, and purified water. For example, in an exemplary embodiment, the eyelid cleanser includes 0.005-0.05% w/w hypochlorous acid, 0.05-5.0% w/w medium chain alkanes, 0.05-3.0% w/w yucca extract, an acidic buffer consisting of 0.001-2.0% w/w sodium acetate and 0.001-2.0% w/w acetic acid, and purified water q.s. up to 100 w/w.

According to an embodiment, an applicator is used to deliver a therapeutically effective amount of an embodiment of the cleanser composition to the ocular area. The applicator can take different forms, including wipes, cloths, pads, sponges, brushes, swabs, puffs, roll-on applicators, and other similar devices. In one specific embodiment, the applicator comprises a hypoallergenic, non-woven, hydrophilic material, which is preferred for its gentle and absorbent properties. The term "pad" refers to a thick piece of fabric that can absorb the active ingredients, such as cotton, cellulose derivatives, polyester, rayon, polypropylene, bamboo, or other suitable materials. The invention encompasses a range of materials and fabrics that can be used for the applicator, including natural or synthetic fibers and non-woven fabrics made from different materials. Overall, the applicator is designed to provide a comfortable and effective way to deliver the cleanser composition to the ocular area.

In one embodiment, the present invention provides a kit for delivering a therapeutically effective amount of an embodiment of the cleanser composition to the ocular area. The kit may include one or more sealed packages, such as sealed pouches, each containing a disposable single-use applicator saturated with an embodiment of the composition. As described herein, the applicator can include a material that is saturated with an embodiment of the composition. Additionally, the kit may include a housing for the packages, along with clear and concise instructions for use.

Experimental Data

Table 1 illustrates the comparative stability of hypochlorous acid in the presence of various ingredients. The inventors determined that only specific ingredients disclosed in the disclosed embodiments are compatible with hypochlorous acid. For example, after 7 days in solution with sodium laureth sulfate, the FAC concentration decreased by about 4% per day. Conversely, immediate degradation of hypochlorous acid was observed with decyl glucoside.

TABLE 1

| Component | Function | [Conc] Tested | FAC Start (ppm) | FAC End (ppm) | Time (days) | % change/day |
|---|---|---|---|---|---|---|
| Citric Acid | Buffer agent | 0.01 M | 188.9 | 5.1 | 2 | −49% |
| Sodium Citrate | Buffer agent | 0.01 M | 125.1 | 2.6 | 2 | −49% |
| Acetic Acid | Buffer agent | 0.01 M | 367.5 | 384.6 | 2 | 2% |
| Sodium Acetate | Buffer agent | 0.01 M | 362.1 | 377 | 2 | 2% |
| Coco Glucoside | Surfactant | 0.50% | 387.6 | 206.3 | 2 | −23% |
| Polysorbate 20 | Surfactant | 0.50% | 391 | 264.9 | 2 | −16% |
| Dioctyl Sulfosuccinate Sodium | Surfactant | 0.50% | 289 | 113 | 10 | −6% |
| Sodium Monobasic Phosphate | Buffer agent | 0.01 M | 361.4 | 374.4 | 2 | 2% |
| Sodium Dibasic Phosphate | Buffer agent | 0.01 M | 250 | 331.1 | 2 | 16% |
| PEG 4000 | Emollient | 1% | 106 | 43 | 3 | −20% |
| Glycerin | Humectant | 1% | 102 | 50 | 3 | −17% |
| Propylene Glycol | Humectant | 1% | 99 | 67 | 3 | −11% |
| Decyl Glucoside | Surfactant | 1% | 3 (immediate degradation) | 0 | 3 | −100% |
| Yucca Extract | Emollient | 0.1% | 188 | 145 | 8 | −3% |
| Polyglyceryl-6 Caprylate and Polyglyceryl-4 Caprate | Surfactant | 0.1% | 146 | 129 | 5 | −2% |
| Caprylyl Capryl Glucoside | Surfactant | 1% | 197 | 109 | 4 | −11% |
| DI-Panthenol | Conditioning agent | 1% | 101 | 23 | 3 | −26% |
| C9-C12 Alkanes | Emollient | 1% | 188 | 184 | 8 | 0% |
| Sodium Laureth Sulfate | Surfactant | 0.5% | 287 | 208 | 7 | −4% |
| Alkyl Olefin Sulfonate | Surfactant | 0.5% | 144 | 47 | 1 | −67% |
| Dioctyl Sulfosuccinate Sodium | Surfactant | 0.5% | 289 | 194 | 38 | −1% |
| Sodium Lauryl Sulfate | Surfactant | 0.5% | 267 | 11 | 238 | 0% |

While the foregoing describes various embodiments of the invention, other and further embodiments of the invention may be devised without departing from the basic scope thereof. The invention is not limited to the described embodiments, versions or examples, which are included to enable a person having ordinary skill in the art to make and use the invention when combined with information and knowledge available to the person having ordinary skill in the art.

The invention claimed is:

1. An eyelid cleanser composition comprising:

0.005 to 0.05 wt. % hypochlorous acid;

0.001 to 2.0 wt. % sodium acetate; and purified water q.s. up to 100% w/w, wherein the composition has a free available chlorine (FAC) concentration of from about 10 ppm-300 ppm.

2. The eyelid cleanser composition according to claim 1, wherein the composition further comprises 0.05 wt. % to 0.75 wt. % sodium lauryl sulfate or sodium laureth sulfate.

3. The eyelid cleanser composition according to claim 2, wherein the composition further comprises 0.001 wt. % to 2.0 wt. % acetic acid.

4. The eyelid cleanser composition according to claim 1, wherein the composition further comprises 0.05 wt. % to 0.75 wt. % capryl/caprylyl glucoside.

5. The eyelid cleanser composition according to claim 4, wherein the composition further comprises 0.05 wt. % to 1.0 wt. % propylene glycol.

6. The eyelid cleanser composition according to claim 5, wherein the composition further comprises 0.001 wt. % to 2.0 wt. % acetic acid.

7. The eyelid cleanser composition according to claim 6, wherein the composition further comprises 0.05 wt. % to 5.0 wt. % medium chain alkanes.

8. The eyelid cleanser composition according to claim 1, wherein the composition further comprises 0.05 wt. % to 0.75 wt. % dioctyl sodium sulfocsuccinate.

9. The eyelid cleanser composition according to claim 8, wherein the composition further comprises 0.001 wt. % to 2.0 wt. % acetic acid.

10. The eyelid cleanser composition according to claim 1, wherein the composition has an osmolality of 40-200 mOsm/kg.

11. The eyelid cleanser composition according to claim 1, wherein the composition has a viscosity of 1 cP-500 cP.

12. The eyelid cleanser composition according to claim 1, wherein the composition has a pH from about 3.5-6.5.

* * * * *